United States Patent [19]

Yoo

[11] 4,450,172

[45] May 22, 1984

[54] ANTIHYPERTENSIVE POLYHALOHYDROXYISOPROPYL PHENYLALKA(E)NOIC ACID ESTERS OF ALKYLAMINOHYDROXYPROPYLOXYPHENYLALKYL ALCOHOLS

[75] Inventor: Sung-eun Yoo, Wilmington, Del.

[73] Assignee: E. I. Du Pont de Nemours and Company, Wilmington, Del.

[21] Appl. No.: 356,712

[22] Filed: Mar. 10, 1982

[51] Int. Cl.³ .................. C07C 69/612; C07C 69/618; A61K 31/235
[52] U.S. Cl. ..................................... 424/309; 424/308; 424/304; 560/17; 560/23; 560/62; 560/45; 260/465 D
[58] Field of Search ....................... 560/23, 60, 62, 17, 560/45; 424/308, 309, 304; 260/465 D

[56] References Cited

U.S. PATENT DOCUMENTS

| 3,236,894 | 2/1966 | England ............................ 560/60 X |
| 3,873,600 | 3/1975 | Brandstrom et al. ............... 260/471 |
| 3,876,802 | 4/1975 | Brandstrom et al. ............... 424/330 |
| 4,199,597 | 4/1980 | Neustadt et al. . |
| 4,311,708 | 1/1982 | Manoury et al. ............... 564/349 X |

Primary Examiner—Bernard Helfin

[57] ABSTRACT

Polyhalohydroxyisopropyl phenylalka(e)noic acid esters of alkylaminohydroxypropyloxyphenylalkyl alcohols, such as 2-(4-((2-hydroxy-3-(1-methylethylamino)-phenyl)ethyl 3-(4-(2,2,2-trifluoro-1-hydroxy-1-trifluoromethylethyl))benzene propanoate, are useful as antihypertensive agents. Preferred compounds give vasodilatory activity and reduced tachycardia.

12 Claims, No Drawings

ANTIHYPERTENSIVE POLYHALOHYDROXYISOPROPYL PHENYLALKA(E)NOIC ACID ESTERS OF ALKYLAMINOHYDROXYPROPYLOXYPHENYLALKYL ALCOHOLS

BACKGROUND OF THE INVENTION

1. Field of Invention

This invention relates to polyhalohydroxyisopropyl phenylalka(e)noic acid esters, processes for their preparation and their uses as antihypertensive agents.

2. Prior Art

Coassigned application Ser. No. 306,411, filed Sept. 28, 1981, describes antihypertensive compounds of the formula:

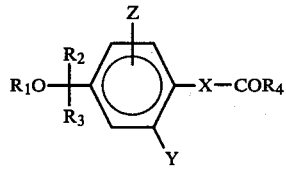

wherein $R_1$ includes H and $C_1$–$C_6$ alkyl;

$R_2$ and $R_3$ are independently $CF_3$, $CF_2Cl$ or $CF_2H$;

X includes —$CH_2CH_2$— or —CH=CH—;

Y and Z include H, $NO_2$ and alkoxy; and $R_4$ includes $NR_6R_7$ and O—$R_5$ where $R_6$ and $R_7$ include H, alkyl, alkylphenyl; and where $R_5$ includes H, alkylphenyl and alkylphenyl with $C_1$–$C_4$ alkoxy substituted on the ring.

U.S. Pat. No. 3,873,600, issued Mar. 25, 1975 and U.S. Pat. No. 3,876,802, issued Apr. 8, 1975, describe para-substituted phenoxy-hydroxypropylamines as β-blockers useful in the treatment of cardiovascular diseases. These compounds have the formula:

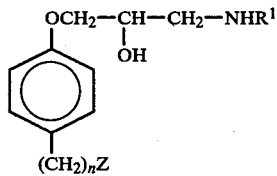

where $R^1$ is i-propyl or t-butyl;

n is 1–3; and

Z includes OR″ or COOR″ where R″ is alkyl of 1–3 carbons.

Many current antihypertensive agents produce unwanted side effects because of undesirable mechanisms of action. For example, mecamylamine is a ganglion blocker, phenoxybenzamine is an α-adrenergic receptor blocker, reserpine is a catecholamine depletor, and asthma is a contraindication for heart disease treatment with the known β-receptor blocking substances such as propanolol, alprenolol and oxyprenolol. There is a constant need for antihypertensive agents which do not produce these side effects, which have fewer side effects, or which minimize such adverse side effects.

SUMMARY OF THE INVENTION

According to the present invention there is provided a compound having the formula:

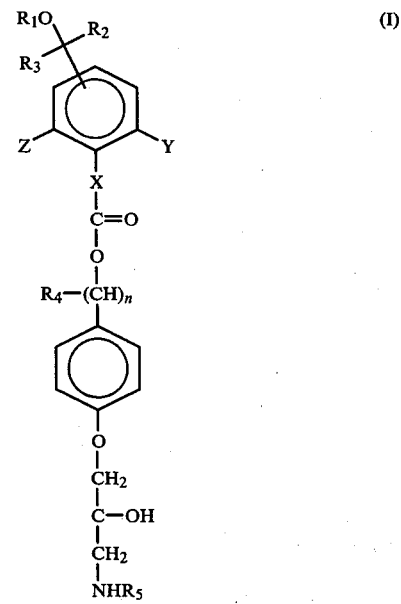

wherein $R_1$ is H, alkyl of 1–6 carbon atoms, acyl of 2–12 carbon atoms, benzoyl, benzyl, or benzyl or benzoyl monosubstituted with CN, $OCH_3$ or Cl;

$R_2$ and $R_3$ are independently $CF_3$, $CF_2Cl$ or $CF_2H$;

Y and Z are independently H, $NO_2$, alkoxy of 1–3 carbon atoms, alkylthio of 1–3 carbon atoms, halo(Cl, Br, F), dialkylamino of 1–3 carbon atoms, alkyl of 1–4 carbon atoms, or $CF_3$;

X is

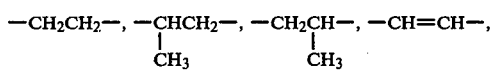

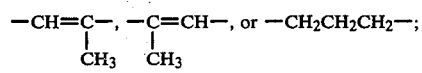

n is 0, 1, 2, or 3;

$R_4$ is H, alkyl of 1–7 carbon atoms, $CF_3$, or aralkyl where the alkyl is 1–7 carbon atoms;

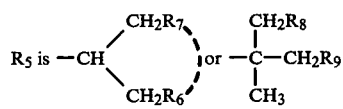

where $R_6$, $R_7$, $R_8$ and $R_9$ are independently H, alkyl of 1–4 carbon atoms, phenyl, phenyl monosubstituted with CN, $OCH_3$ or Cl, benzyl, or benzyl monosubstituted with CN, $OCH_3$ or Cl; or $R_6$ and $R_7$ taken together are $(CH_2)_m$ where m is 0, 1, 2 or 3;

or a pharmaceutically acceptable salt thereof.

There is also provided a pharmaceutical composition containing an effective antihypertensive amount of at least one of the above-mentioned compounds, and a method of using the compounds to treat hypertension in a mammal.

Further provided is a process for preparing one of the above-mentioned compounds comprising: contacting and reacting an epoxide compound of the formula:

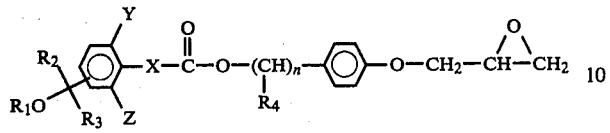

wherein $R_1$, $R_2$, $R_3$, Y, Z, n and $R_4$ are as defined in claim 1, with an amine of the formula:

$NH_2-R_5$ where $R_5$ is as defined in claim 1.

DETAILED DESCRIPTION OF THE INVENTION

Preferred Compounds

Compounds of Formula I that are preferred for antihypertensive activity are those wherein, independently;
$R_1$ is H;
$R_2$ and $R_3$ are $CF_3$;
Y is H or $NO_2$;
Z is H;
X is

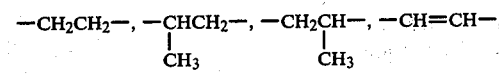

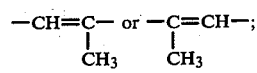

n is 2;
$R_4$ is H; or

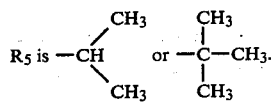

Most preferred compounds of Formula I because of their vasodilatory activity with reduced tachycardia are compounds where:
$R_1$ is H;
$R_2$ and $R_3$ are $CF_3$;
Y is H or $NO_2$;
Z is H;
X is

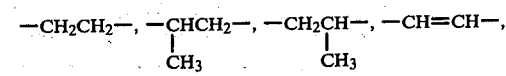

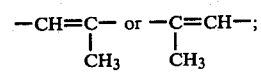

n is 2;
$R_4$ is H; and

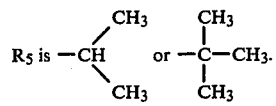

DETAILED DESCRIPTION OF THE INVENTION

Pharmaceutical Salts

Pharmaceutically suitable salts and their preparation are well known to those skilled in pharmaceuticals and any can be used in the present invention. Suitable salts include acid addition salts, preferably formed from organic acids such as fumaric acid and maleic acid and mineral acids such as hydrochloride, nitrate and sulfate. The acid used preferably has a pKa of not greater than 2.5.

Synthesis

The compounds of Formula I are prepared by the process illustrated in Reaction I.

Reaction I

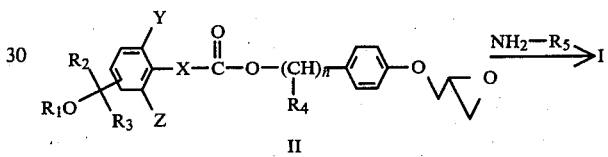

The compounds of Formula I are prepared by reacting an ester-epoxide (II) with an appropriate amine, such as isopropylamine or t-butylamine as illustrated in Reaction I. The reaction can be performed neat or in aprotic or protic solvents such as methanol, ethanol, toluene, benzene, acetonitrile or methylene chloride within a temperature range of from room temperature to the reflux temperature of any solvent employed.

The ester-expoxide (II) used in Reaction I can be prepared by several methods which are outlined below in Reactions II and III.

Reaction II

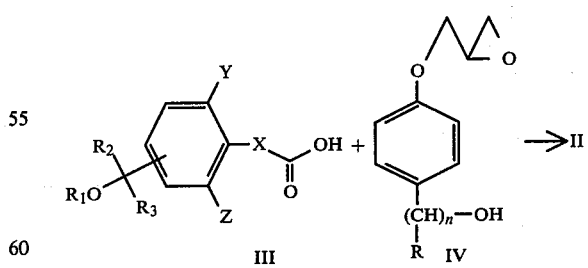

In Reaction II, an acid (III) is coupled with an epoxy-alcohol (IV) by coupling reagents such as dicyclohexylcarbodiimide, EEDQ (N-ethoxycarbonyl-2-ethoxy-1,2-dihydroquinoline) and Woodward reagent, etc. (Greenstein, J. P., and M. Winitz, "Chemistry of the Amino Acid", Vol. III, John Wiley and Sons, Inc., 1961).

Reaction III

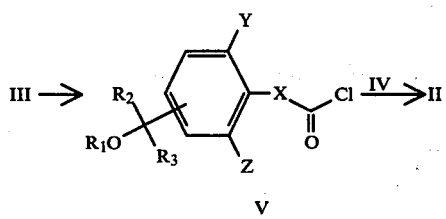

In Reaction III, a carboxylic acid (III) is converted to the corresponding acid chloride of Formula V by reacting with oxalyl chloride or thionyl chloride in an inert solvent, such as, but not limited to, toluene, benzene, methylene chloride, tetrahydrofuran or dimethylformamide. The reaction may be run at room temperature to the reflux temperature of the solvent.

The acid chloride (V) is then reacted with the epoxy-alcohol (IV) in the presence of a non-nucleophilic base to yield the desired product of Formula II. An aprotic solvent such as toluene, benzene, methylene chloride, tetrahydrofuran (THF) or dimethylformamide (DMF) can be used. Suitable non-nucleophilic bases include, among others, triethylamine, diisopropylethylamine and p-dimethylaminopyridine.

Alternatively, the carboxylic acid of Formula III can be activated, prior to reaction with the epoxy-alcohol (IV), by a known procedure involving formation of a mixed anhydride or active ester (Greenstein, J. P., and M. Winitz, "Chemistry of the Amino Acid", Vol. III, John Wiley and Sons, Inc., 1961).

The epoxy-alcohol (IV) used in Reactions II and III can be prepared from an appropriate p-hydroxyphenalkyl alcohol as follow:

Reaction IV

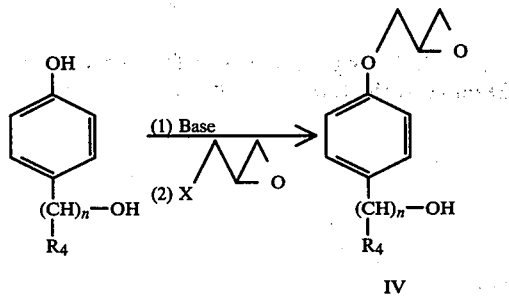

In Reaction IV, a p-hydroxyphenalkyl alcohol is treated with a base such as sodium hydride or sodium ethoxide and then reacted with an epihalohydrin. The reaction may be run in a solvent such as dimethylformamide, toluene, benzene, tetrahydrofuran or methylene chloride at a temperature in the range of from $-20°$ C. to a solvent reflux temperature but preferably at room temperature.

Alternatively, the epoxy-alcohol IV can be prepared in two steps as shown in Reaction V.

Reaction V

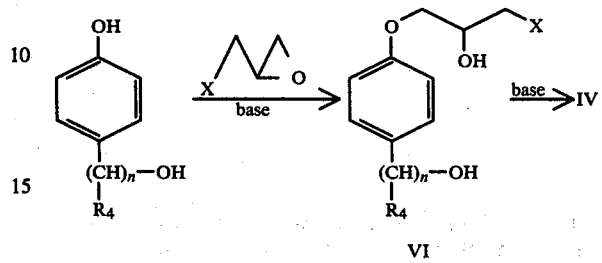

The reaction of a p-hydroxyphenalkyl alcohol with an epihalohydrin in the presence of a base such as piperidine, pyrrolidine, p-dimethylaminopyridine, pyridine and alkaline hydroxide yields a halohydrin of Formula VI which can be treated with a base such as sodium hydride, sodium alkoxide or alkaline hydroxide to yield the epoxy-alcohol (IV).

The acids of Formula III used in Reactions II and III can be prepared as described in the aforesaid copending U.S. application Ser. No. 306,411, filed Sept. 28, 1981 (BP-6169-A).

The product of Formula I may have more than one asymmetric centers and thus may exist as distereomeric forms or as racemic mixtures. All such isomers are included in the scope of the invention.

The compounds of Formula I can form salts with various organic and inorganic acids. These acids include fumaric acid, maleic acid, benzoic acid, hydrochloric acid, nitric acid and sulfuric acid. Non-toxic, pharmaceutically acceptable salts are preferred but other salts are useful for isolating and/or purifying the intermediate and final product.

In the following examples, temperatures are in degrees Centigrade.

EXAMPLE 1

2-(4-((2-Hydroxy-3-(1-methylethylamino)phenyl)ethyl 3-(4-(2,2,2-trifluoro-1-hydroxy-1-trifluoromethylethyl)-)benzenepropanoate, Fumarate Salt

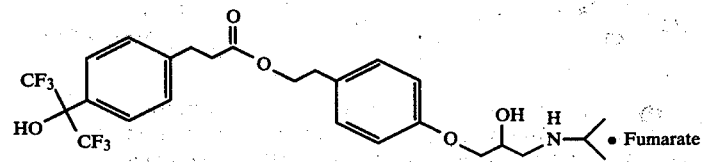

A solution of 3-(4-(2,2,2-trifluoro-1-hydroxy-1-trifluoromethylethyl))benzenepropanoic acid (9.5 g) in 90 ml of methylene chloride was treated with 4-(2,3-epoxypropyloxy)phenethyl alcohol (5.8 g), 0.2 g of dimethylaminopyridine and 6.8 g of dicyclohexylcarbodiimide. The reaction mixture was stirred at room temperature for 20 hours.

The insoluble material was removed by filtration and the filtrate was concentrated in vacuo to give a crude product which was purified by column chromatography (hexane:ethyl acetate, 1:1).

The fractions containing the desired product were concentrated in vacuo to give a thick, colorless oil (10 g) which was dissolved in 50 ml of isopropylamine. The reaction mixture was refluxed under nitrogen for 48 hours. The reaction mixture was concentrated to give a desired compound as a foam (11 g).

The resulting free amine was converted to the fumaric acid salt by dissolving in acetonitrile and treatment with 1 equivalent of fumaric acid. The mixture was refluxed briefly, cooled with ice and the crystallization was completed by the addition of diethyl ether. The resulting white crystals were collected by filtration and dried in vacuo, m.p. 172°–173°, yield 11 g.
NMR (DMSO-d$_6$)δ:
 1.3 (d, 6H);
 2.5~3.5 (m, 9H);
 3.9~4.4 (m, 4H);
 6.7 (s, 2H); and
 6.8~7.8 (m, 8H).
Mass spec. 551 (M+)

EXAMPLE 2

2-(4-((2-Hydroxy-3-(1-methylethylamino)phenyl)ethyl 3-(2-nitro-4-(2,2,2-trifluoro-1-hydroxy-1-trifluoromethylethyl)benzenepropanoate, Fumarate Salt

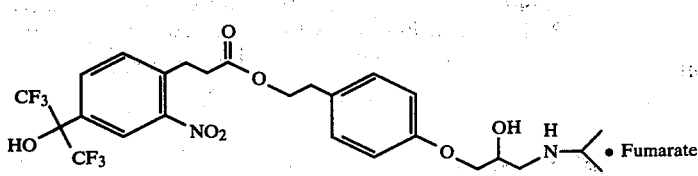

By substituting 3-(2-nitro-4-(2,2,2-trifluoro-1-hydroxy-1-trifluoromethylethyl)benzenepropanoic acid for 3-(4-(2,2,2-trifluoro-1-hydroxy-1-trifluoromethylethyl)benzenepropanoic acid in Example 1, the free amine of the title compound was obtained as a colorless foam, yield, 65%.

The fumarate salt of the title compound was obtained by the method described in Example 1 as a colorless solid, m.p. 174°–176°.
NMR (DMSO-d$_6$)δ:
 1.35 (d×d, 6H);
 2.7~4.4 (m, 14H);
 6.8 (s, 2H); and
 6.8~7.4 (m, 7H).
Mass spec. 581 (M+—CH$_3$)

EXAMPLE 3

2-(4-((2-Hydroxy-3-(1,1-methylethylamino)phenyl)ethyl 3-methyl-3-(4-(2,2,2-trifluoro-1-hydroxy-1-trifluoromethylethyl))benzenepropanoate, Fumaric Salt

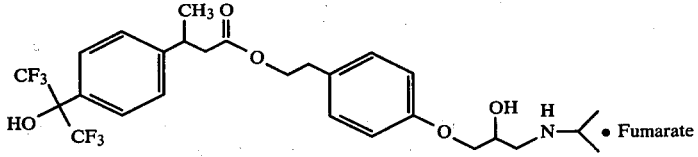

By following the procedure described in Example 1, the diastereoisomeric mixture of the title compound was obtained as a colorless foam, yield 67%.

The fumarate salt of the title compound was obtained as a colorless solid, m.p. 95°–105°.
NMR (CDCl$_3$:DMSO-d$_6$)δ:
 1.2~1.4 (m, 9H);
 2.5~4.3 (m, 13H);
 6.6 (s, 2H); and
 6.7~7.7 (m, 8H).
Mass spec. 565 (M+)

EXAMPLE 4

2-(4-((2-Hydroxy-3-(1,1-dimethylethylamino)phenyl)-ethyl 3-(4-(2,2,2-trifluoro-1-hydroxy-1-trifluoromethyl)ethyl)benzenepropanoate, Fumarate Salt

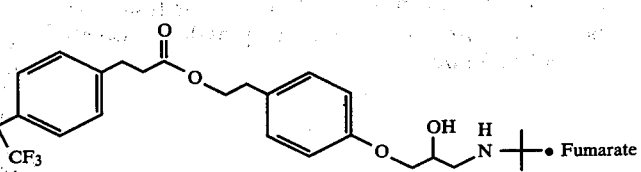

By substituting t-butylamine for isopropylamine in Example 1, the title compound as a fumurate salt was obtained as a colorless solid, m.p. 188°–190°.
NMR (DMSO-d$_6$)δ:
 1.22 (s, 9H);
 2.5~3.0 (m, 8H);
 4.0~4.4 (m, 5H);
 5.4 (broad s);
 6.5 (s, 2H); and
 6.8~7.8 (m, 8H).
Mass spec. 550 (M+—CH$_3$), 86 (base peak)

EXAMPLE 5

2-(4-((2-Hydroxy-3-(1,1-dimethylethylamino)phenyl)-ethyl 3-(2-methoxy-4-(2,2,2-trifluoro-1-hydroxy-1-trifluoromethylethyl)benzenepropanoate, Fumarate Salt

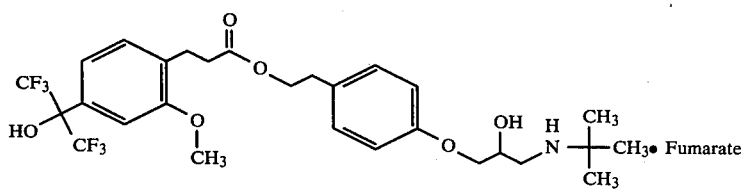

By substituting 3-(2-methoxy-4-(2,2,2-trifluoro-1-hydroxy-1-trifluoromethylethyl)benzenepropanoic acid for 3-(4-(2,2,2-trifluoro-1-hydroxy-1-trifluoromethylethyl)benzenepropanoic acid and t-butylamine for isopropylamine in Example 1, the free amine of the title compound was obtained as a foam.

The fumarate salt of the title compound was obtained by the method described in Example 1 as a colorless solid, m.p. 145°–150°.

Preparation of Intermediates 2,3-Epoxypropyl p-β-hydroxyethylphenyl ether

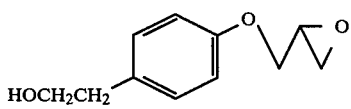

To 100 ml of ice-cooled methanol was added 2.3 g of sodium portionwise. After all of the sodium reacted, 13.8 g of p-hydroxyphenethyl alcohol was added slowly to the above sodium methoxide solution.

The resulting dark brownish solution was concentrated in vacuo. The resulting residue was dissolved in 100 ml of dried DMF to which was added 9.5 ml of epibromohydrin and 0.1 g of sodium iodide. The reaction mixture was then stirred at room temperature under nitrogen for 24 hours. Excess DMF was evaporated under reduced pressure and the residue was dissolved in 300 ml of ethyl acetate. The ethyl acetate solution was washed with water, dried over anhydrous MgSO$_4$ and concentrated to give a oily residue which was purified by column chromatography (CH$_2$Cl$_2$:ethyl acetate, 1:1 elution). The fractions containing the product were concentrated in vacuo to give a colorless solid, 11.5 g (yield 63%) m.p. 58°–61°.

NMR (CDCl$_3$)δ:
2.5–3.0 (m, 4H);
3.1–3.5 (m, 1H);
3.6–4.4 (m, 4H); and
6.7~7.2 (q, 4H).

By following the procedures described, the compounds listed in Table I can be prepared.

TABLE 1

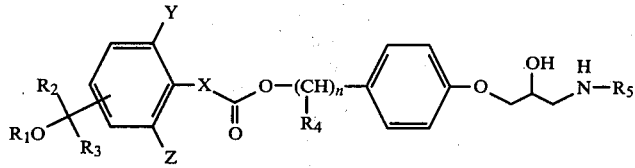

| R$_1$ | R$_2$ | R$_3$ | Y | Z | X | n | R$_4$ | R$_5$ |
|---|---|---|---|---|---|---|---|---|
| H | CF$_3$ | CF$_3$ | H | H | —CH=CH— | 2 | H | —CH(CH$_3$)$_2$ |
| H | CF$_3$ | CF$_3$ | H | H | —C(CH$_3$)=CH— | 2 | H | —CH(CH$_3$)$_2$ |
| H | CF$_3$ | CF$_3$ | H | H | —CH=C(CH$_3$)— | 2 | H | —CH(CH$_3$)$_2$ |
| H | CF$_3$ | CF$_3$ | OCH$_3$ | H | —CH$_2$CH$_2$— | 2 | H | —CH(CH$_3$)$_2$ |
| H | CF$_3$ | CF$_3$ | OCH$_3$ | H | —CH=CH— | 2 | H | —CH(CH$_3$)$_2$ |
| H | CF$_3$ | CF$_3$ | CH$_3$ | H | —CH$_2$CH$_2$— | 2 | H | —CH(CH$_3$)$_2$ |
| H | CF$_3$ | CF$_3$ | CF$_3$ | H | —CH$_2$CH$_2$— | 2 | H | —CH(CH$_3$)$_2$ |
| H | CF$_3$ | CF$_3$ | SCH$_3$ | H | —CH$_2$CH$_2$— | 2 | H | —CH(CH$_3$)$_2$ |
| H | CF$_3$ | CF$_3$ | N(CH$_3$)$_2$ | H | —CH$_2$CH$_2$— | 2 | H | —CH(CH$_3$)$_2$ |
| H | CF$_3$ | CF$_3$ | Cl | H | —CH$_2$CH$_2$— | 2 | H | —CH(CH$_3$)$_2$ |
| H | CF$_3$ | CF$_3$ | OCH$_3$ | NO$_2$ | —CH$_2$CH$_2$— | 2 | H | —CH(CH$_3$)$_2$ |
| H | CF$_3$ | CF$_3$ | NO$_2$ | NO$_2$ | —CH$_2$CH$_2$— | 2 | H | —CH(CH$_3$)$_2$ |
| H | CF$_3$ | CF$_3$ | Cl | Cl | —CH$_2$CH$_2$— | 2 | H | —CH(CH$_3$)$_2$ |
| H | CF$_3$ | CF$_3$H | H | H | —CH$_2$CH$_2$— | 2 | H | —CH(CH$_3$)$_2$ |
| H | CF$_3$ | CF$_2$Cl | H | H | —CH$_2$CH$_2$— | 2 | H | —CH(CH$_3$)$_2$ |
| H | CF$_2$H | CF$_2$H | H | H | —CH$_2$CH$_2$— | 2 | H | —CH(CH$_3$)$_2$ |
| H | CF$_2$Cl | CF$_2$Cl | H | H | —CH$_2$CH$_2$— | 2 | H | —CH(CH$_3$)$_2$ |
| CH$_3$ | CF$_3$ | CF$_3$ | OCH$_3$ | H | —CH$_2$CH$_2$— | 2 | H | —CH(CH$_3$)$_2$ |
| φ-CH$_2$— | CF$_3$ | CF$_3$ | OCH$_3$ | H | —CH$_2$CH$_2$— | 2 | H | —CH(CH$_3$)$_2$ |
| φ−C(O)− | CF$_3$ | CF$_3$ | OCH$_3$ | H | —CH$_2$CH$_2$— | 2 | H | —CH(CH$_3$)$_2$ |
| φ−C(O)− | CF$_3$ | CF$_3$ | OCH$_3$ | H | —CH=CH— | 2 | H | —CH(CH$_3$)$_2$ |

TABLE 1-continued

Structure: R1O-[phenyl with R2, R3, Y, Z substituents]-X-C(=O)-O-(CH)n(R4)-[phenyl]-O-CH2-CH(OH)-CH2-NH-R5

| R1 | R2 | R3 | Y | Z | X | n | R4 | R5 |
|---|---|---|---|---|---|---|---|---|
| φ-C(=O)- | CF$_3$ | CF$_3$ | NO$_2$ | H | —CH=CH— | 2 | H | —CH(CH$_3$)$_2$ |
| CH$_3$-C(=O)- | CF$_3$ | CF$_3$ | OCH$_3$ | H | —CH=CH— | 2 | H | —CH(CH$_3$)$_2$ |
| CH$_3$-C(=O)- | CF$_3$ | CF$_3$ | NO$_2$ | H | —CH$_2$CH$_2$— | 2 | H | —CH(CH$_3$)$_2$ |
| H | CF$_3$ | CF$_3$ | H | H | —CH$_2$CH$_2$— | 0 | — | —CH(CH$_3$)$_2$ |
| H | CF$_3$ | CF$_3$ | H | H | —CH$_2$CH$_2$— | 1 | H | —CH(CH$_3$)$_2$ |
| H | CF$_3$ | CF$_3$ | H | H | —CH$_2$CH$_2$— | 3 | H | —CH(CH$_3$)$_2$ |
| H | CF$_3$ | CF$_3$ | H | H | —CH$_2$CH$_2$— | 2 | CH$_3$ | —CH(CH$_3$)$_2$ |
| H | CF$_3$ | CF$_3$ | H | H | —CH$_2$CH$_2$— | 2 | CF$_3$ | —CH(CH$_3$)$_2$ |
| H | CF$_3$ | CF$_3$ | H | H | —CH$_2$CH$_2$— | 2 | —CH$_2$φ | —CH(CH$_3$)$_2$ |
| H | CF$_3$ | CF$_3$ | H | H | —CH$_2$CH$_2$— | 2 | H | —CH(CH$_3$)CH$_2$φ |
| H | CF$_3$ | CF$_3$ | H | H | —CH$_2$CH$_2$— | 2 | H | —C(CH$_3$)$_2$CH$_2$φ |
| H | CF$_3$ | CF$_3$ | H | H | —CH$_2$CH$_2$— | 2 | H | —CH(CH$_3$)CH$_2$CH$_2$φ |
| H | CF$_3$ | CF$_3$ | H | H | —CH$_2$CH$_2$— | 2 | H | —C(CH$_3$)$_2$CH$_2$CH$_2$φ |
| H | CF$_3$ | CF$_3$ | NO$_2$ | H | —CH$_2$CH$_2$— | 2 | H | —C(CH$_3$)$_3$ |

Dosage

The compounds of this invention can be administered in the treatment of hypertension according to the invention by any means that effects contact of the active ingredient compound with the site of action in the body of a warm-blooded animal. For example, administration can be parenteral, i.e., subcutaneous, intravenous, intramuscular, or intraperitoneal. Alternatively or concurrently, administration can be by the oral route.

For the purpose of this disclosure, a warm-blooded animal is a member of the animal kingdom possessed of a homeostatic mechanism and includes mammals and birds.

The dosage administered will be dependent on the age, health and weight of the recipient; the extent of disease, kind of concurrent treatment, if any, frequency of treatment and the nature of the effect desired. Dosages as high as 100 milligrams per kilogram of body weight can be used. Usually, a daily dosage of active ingredient compound will be from about 0.01 to 50 milligrams per kilogram of body weight. Ordinarily, from 0.05 to 40, and preferably 0.1 to 20, milligrams per kilogram per day in one or more applications per day is effective to obtain desired results. For the more potent compounds of the invention, e.g., methyl 2-methoxy-4-[2,2,2-trifluoro-1-hydroxy-1-(trifluoromethyl)ethyl]-phenylpropanoate, the daily dosage ranges are from about 0.01 to 10 mg/kg, preferably 0.05 to 10 mg/kg, and more preferably 0.05 to 5 mg/kg.

Dosage forms (compositions) suitable for internal administration contain from about 0.1 milligrams to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules can contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used as citric acid and its salts and sodium EDTA. In addition parenteral solutions can contain preservatives, such as benzalkonium chloride, methyl- or propyl-paraben, and chlorobutanol.

Suitable pharmaceutical carriers are described in Remington's Pharmaceutical Sciences, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 50 milligrams of powdered active ingredient, 175 milligrams of lactose, 24 milligrams of talc, and 6 milligrams magnesium stearate.

Capsules

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 225 milligrams of lactose. Appropriate coatings may be applied to increase palatability or delay absorption.

Injectable

A parenteral composition suitable for administration by injection is prepared by stirring 1.5% by weight of active ingredient in 10–60% by volume of co-solvents, like propylene glycol in water. The resultant solution can be sterilized by filtration.

Suspension

An aqueous suspension is prepared for oral administration so that each 5 milliliters contain 10 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Injectable

A parenteral composition suitable for administration by injection is prepared by dissolving 1% by weight of active ingredient in sodium chloride injection U.S.P. XV and adjusting the pH of the solution to between 6 and 7. The solution can be sterilized by filtration.

Utility

The antihypertensive activity of the compounds of this invention is evidenced by tests conducted in hypertensive rats. In these tests, rats are made hypertensive by subcutaneous implantation of pellets of desoxycorticosterone acetate (DOCA) and by giving the rats saline solution to drink essentially according to the method described by Sturtevant (Annals of Internal Medicine, 49, 1281 [1958]). Graded dose levels of each compound are administered orally to groups of 8 hypertensive rats. The compound is prepared in an aqueous polyvinyl alcohol/acacia vehicle and administered at a volume to body weight ratio of 5.0 ml/kg. Sixteen hypertensive rats receiving the aqueous vehicle by the same route serve as controls for each test. At various intervals of time after treatment, usually 90 minutes, the systolic arterial blood pressure of each rat is determined by modification of the microphone-manometer technique (Friedman, M. and Freed, S. C., Proc. Soc. Exp. Biol. and Med., 70, 670 [1949]). That dose of compound which produces a 30 mm mercury (mm Hg) reduction in blood pressure when compared to the mean systolic arterial blood pressure of the control animals is then determined (Effective Dose 30). For example, an ED30 of 12 mg/kg orally was obtained with the compound of Example 1. An ED30 of 15 mg/kg was obtained with the compound of Example 2. Biological results are shown in Table 2.

TABLE 2

| Effects on Systolic Arterial Blood Pressures of DOCA - Hypertensive Rats | |
|---|---|
| Example No. | ED$_{30}$ mg/kg p.o. |
| 1 | 12 |
| 2 | 15 |
| 3 | −43 mm Hg (50 mg/kg) |
| 4 | −30 mm Hg (50 mg/kg) |
| 5 | 0.85 (with slight increase in heart rate) |

What is claimed is:

1. A compound having the formula:

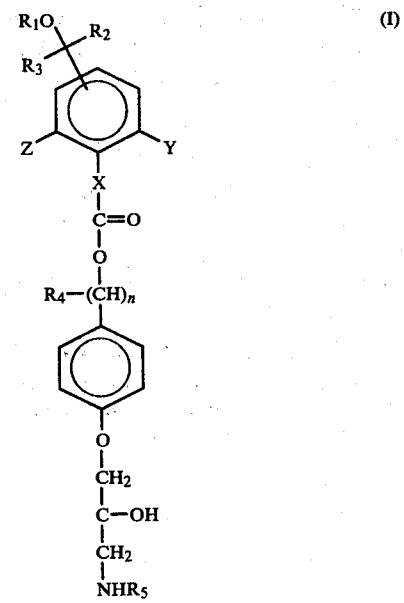

wherein

R$_1$ is H, alkyl of 1–6 carbon atoms, acyl of 2–12 carbon atoms, benzoyl, benzyl, or benzyl or benzoyl monosubstituted with CN, OCH$_3$ or Cl;

R$_2$ and R$_3$ are independently CF$_3$, CF$_2$Cl or CF$_2$H;

Y and Z are independently H, NO$_2$, alkoxy of 1–3 carbon atoms, alkylthio of 1–3 carbon atoms, halo(Cl, Br, F), dialkylamino of 1–3 carbon atoms, alkyl of 1–4 carbon atoms, or CF$_3$;

X is

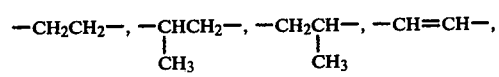

-continued

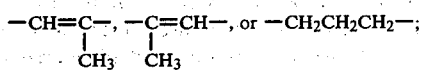

$n$ is 0, 1, 2, or 3;

$R_4$ is H, alkyl of 1-7 carbon atoms, $CF_3$, or aralkyl where the alkyl is 1-7 carbon atoms;

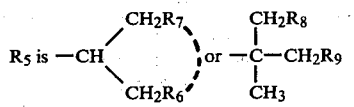

where $R_6$, $R_7$, $R_8$ and $R_9$ are independently H, alkyl of 1-4 carbon atoms, phenyl, phenyl monosubstituted with CN, $OCH_3$ or Cl, benzyl, or benzyl monosubstituted with CN, $OCH_3$ or Cl; or $R_6$ and $R_7$ taken together are $(CH_2)_m$ where m is 0, 1, 2 or 3;

or a pharmaceutically acceptable salt thereof.

2. The compound of claim 1 wherein $R_1$ is H.
3. The compound of claim 1 wherein $R_2$ and $R_3$ are $CF_3$.
4. The compound of claim 1 wherein Y is H or $NO_2$.
5. The compound of claim 1 wherein Z is H.
6. The compound of claim 1 wherein X is

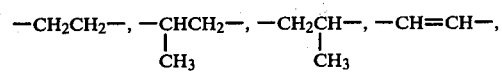

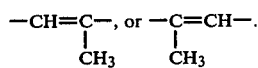

7. The compound of claim 1 wherein n is 2.
8. The compound of claim 1 wherein $R_4$ is H.
9. The compound of claim 1 wherein

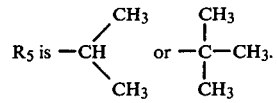

10. A compound of the formula:

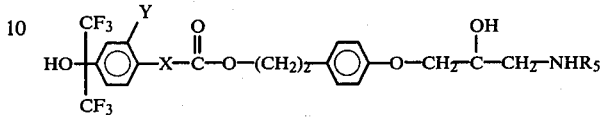

wherein
Y is N or $NO_2$;
X is

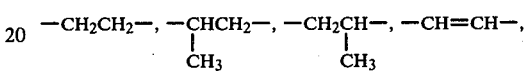

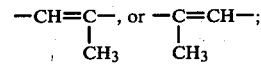

$R_5$ is

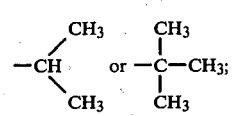

a pharmaceutically acceptable salt thereof.

11. A pharmaceutical composition consisting essentially of an antihypertensive amount of a compound of claim 1 or claim 2 or claim 3 or claim 4 or claim 5 or claim 6 or claim 7 or claim 8 or claim 9 or claim 10 and a pharmaceutically acceptable carrier.

12. A method of treating hypertension in a mammal consisting essentially of administering to a hypertensive mammal an antihypertensive amount of a compound of claim 1 or claim 2 or claim 3 or claim 4 or claim 5 or claim 6 or claim 7 or claim 8 or claim 9 or claim 10.

* * * * *